United States Patent [19]

Riazi

[11] Patent Number: 5,104,317
[45] Date of Patent: Apr. 14, 1992

[54] ELASTOMERIC CORD FOR RETAINING A DENTAL DAM, CORD DISPENSER AND RELATED COMBINATIONS AND METHODS

[75] Inventor: John Riazi, Akron, Ohio

[73] Assignee: The Hygenic Corporation, Akron, Ohio

[21] Appl. No.: 578,424

[22] Filed: Sep. 6, 1990

[51] Int. Cl.$^5$ .......................... A61C 5/14; A61C 5/12
[52] U.S. Cl. ...................................... 433/136; 433/138
[58] Field of Search ................ 433/40, 136, 138, 139, 433/140

[56] References Cited

U.S. PATENT DOCUMENTS

| | | | |
|---|---|---|---|
| 484,046 | 10/1892 | Pitman | 433/136 |
| 806,300 | 12/1905 | Sorenson | 433/138 X |
| 1,031,533 | 7/1912 | Davison | 433/139 |
| 1,973,615 | 9/1934 | Eustis | 433/136 X |
| 3,238,620 | 3/1966 | Robertson | 433/40 |
| 4,465,462 | 8/1984 | Ticknor | 433/136 |
| 4,522,593 | 6/1985 | Fischer | 433/136 |

FOREIGN PATENT DOCUMENTS

3122834  12/1982  Fed. Rep. of Germany ...... 433/136

*Primary Examiner*—Robert P. Swiatek
*Assistant Examiner*—Nicholas D. Lucchesi
*Attorney, Agent, or Firm*—Renner, Kenner, Greive, Bobak, Taylor & Weber

[57] ABSTRACT

A method for retaining a dental dam comprises the steps of positioning a dental dam (11) over a plurality of teeth in the mouth of a patient; selecting a section of elastomeric cord (10); elongating the section to reduce the cross-sectional area thereof; interposing a portion of the elongated section between at least two adjacent teeth and over the dam; and allowing the section to expand toward its original cross-sectional area thereby prohibiting the removal of the dam from the teeth. Also provided in combination with a dental dam (11) having a plurality of individual holes to fit over a like plurality of teeth in the mouth of a patient, is an elastomeric cord (10) having a first, relaxed diameter and a second elongated diameter of lesser dimension than the first, the second diameter being interposed between a pair of adjacent teeth and over the dam in position with respect to the teeth, wherein the first diameter forms an elastomeric wedge between the teeth to retain the dam. A novel elastomeric cord (10) is provided for retaining a dental dam which is preferably provided in a column (40). A method for manufacturing the column is taught as is the use of such a column in combination with a container (50).

12 Claims, 4 Drawing Sheets

ELASTOMERIC CORD FOR RETAINING A DENTAL DAM, CORD DISPENSER AND RELATED COMBINATIONS AND METHODS

TECHNICAL FIELD

The present invention relates in general to dental dams utilized in the orthodontic and oral surgery fields. More particularly, the present invention relates to a means for more safely and efficiently retaining and stabilizing the dental dam. Specifically, the present invention relates to an improved stabilizing method that does not injure the patients tooth cementum or the gingiva tissue while still providing a clean dry work area for the practitioner. A novel elastomeric cord is employed for retaining the dam which is preferably provided in a column. The present invention also provides for the combination of the cord with the dental dam as well as the combination of the cord with a dispensing container. Finally, the present invention discloses a method for the manufacture of the column.

BACKGROUND OF THE INVENTION

An item employed in many oral surgery and orthodontic procedures is a dental dam. The rubber dental dam is known in the art and has been utilized in dentistry since 1864. It comprises a thin flexible piece of rubber employed to isolate one or more teeth during various dental procedures. The purpose for using the rubber dental dam is to provide an optimum working environment for the dentist while protecting the patient during operative procedures.

The dam not only eliminates saliva from the field of operation, but also mildly retracts the soft tissue around the tooth, particularly when the operative procedure is a class V type operation. Most procedures in operative dentistry are performed more efficiently by employing a dental dam as it assures a dry working area during all steps of the procedure. This is particularly true when an operation is on a carious lesion where the pulp may be exposed; the dental dam then minimizes pulpal contamination. Another advantage to operating in a dry field is that dental restorative materials do not develop their full properties in a wet operating environment. The rubber dam then permits a dentist to obtain the expected physical properties of materials because of the dry field.

The dental dam also protects the patient and the practitioner. The rubber dental dam protects the patient from the possibility of aspirating or swallowing debris. Also, the dam will permit prompt recovery of small instruments such as thin files dropped during the operative procedure. The dental dam also affords the practitioner protection from any infectious disease that may be present in the patient's mouth.

To employ a dental dam, the dam can first be placed around and attached to, a Young holder; which is a frame for the dental dam. Holes are subsequently punched in the dam such that each hole corresponds to a tooth that will be placed therethrough. The dental dam is then lubricated to facilitate the passing of the dam through the tooth crown contact points. Alternatively, the holes are punched first, the dam is installed over the teeth and is then stretched over the frame. In either order, the dental dam then must be stabilized by a retainer means.

The retainer clamp is the most common prior art form of stabilizing a dental dam and consists of four prongs and two jaws connected by a bow. The problem with utilizing a retainer clamp is that the clamp is not ideally configured for a specific tooth. Due to the variation in teeth across a single mouth, from sharp thin incisors to broad wide molars, many type of teeth are encountered. Further, every mouth has different sizes and shapes of teeth. As a result, with specific clamps designed for specific teeth, many types of retainer clamps need to be stocked by the practitioner.

Another disadvantage in employing the dental dam retainer clamp is that the four prongs must contact the tooth, if they do not, the clamp may need to be ground, a process requiring still more time. Furthermore, even with four point contact, the retainer can injure the gingiva, as well as the tooth, resulting in post-operative soreness. Accurate placement of the clamps is difficult to achieve and as a result, the patient may need to be anesthetized allowing for more comfortable retainer placement on the anchor tooth. The clamp may also create sealing problems on the anchor tooth which then creates leakage problems of wetness into the work area.

To correct this and the problems discussed above, some dentists place dental tape or floss around the tooth gingival and tie a surgeon's knot, as is well known in the art. While this method is effective, it is time consuming and requires a skilled dentist to employ. However, often a dental assistant installs the dental dam, thereby making this method ineffective.

To cure this problem, a simpler method has been employed. That method is to cut away a corner of the dental dam, roll it, and place the rolled portion into a diastema to serve as an anterior anchor. However, one will note that this method not only requires cutting the dam, but also would not be feasible in a narrow space. A diastema is a necessity as the unit employed as the anchor is very wide. A further problem with this method is that the retainer is obtrusive in an obviously small work area.

SUMMARY OF THE INVENTION

It is therefore a primary object of the present invention to provide a simplified means for retaining a dental dam.

It is another object of the present invention to provide a retaining method, as above, which incorporates an uncomplicated arrangement by which to secure a dry working environment while supplying a pre-formed anterior anchor that is easy to install.

It is still another object of the present invention to provide a retaining method for retaining a dental dam without injuring the tooth or the gingiva tissue.

It is yet another object of the present invention to provide a retaining method wherein a minimal number of devices need be stocked to accommodate all the tooth arrangements encountered.

It is a further object of the present invention to provide a retaining method for a dental dam that provides a thin member to fit slidably between the tooth crown contact point then, upon sliding through the contact point, the member expands to fill the void between the two teeth and the gingival mucosa thereby creating a full retention apparatus.

It is still a further object of the present invention to provide in combination, a dental dam and elastomeric cord.

It is a further object of the present invention to provide novel forms of elastomeric cord for use in retaining a dental dam.

It is a further object of the present invention to provide a dispenser containing the elastomeric cord in a manner for cord withdrawal without entanglement.

These and other objects of the invention, as well as the advantages thereof over existing and prior art forms, which will be apparent in view of the detailed specification, are accomplished by means hereinafter described and claimed.

In general, the present invention provides a method for retaining a dental dam which comprises the steps of positioning a dental dam over a plurality of teeth in the mouth of a patient; selecting a section of elastomeric cord; elongating the section to reduce the cross-sectional area thereof; interposing a portion of the elongated section between at least two adjacent teeth and over the dam; and allowing the section to expand toward its original cross-sectional area thereby prohibiting the removal of the dam from the teeth.

The present invention also provides, in combination with a dental dam having a plurality of individual holes to fit over a like plurality of teeth in the mouth of a patient, an elastomeric cord having a first, relaxed diameter and a second elongated diameter of lesser dimension than the first, the second diameter being interposed between a pair of adjacent teeth and over the dam in position with respect to the teeth, wherein the first diameter forms an elastomeric wedge between the teeth to retain the dam.

The present invention also provides an article for use in retaining a dental dam comprising an elastomeric cord having a first, relaxed diameter and a second elongated diameter of lesser dimension than the first, the second diameter being interposable between a pair of adjacent teeth and the first diameter forming an elastomeric wedge between the teeth.

Further provided is a method for manufacturing a webbed column of elastomeric cord which comprises the steps of winding uncured elastomeric cord around a mandrel in continuous fashion assuring that each successive winding is contiguous with the adjacent windings curing the uncured rubber whereby the contiguous windings adhere to each other, creating a web therebetween; and removing the column from the mandrel.

A column of elastomeric cord is also provided and comprises a continuous length of the elastomeric cord having at least one free end and forming a continuous helix having a pitch substantially equal to the diameter of the cord, thereby defining a plurality of adjacent windings, with the windings being connected to each other to form a web.

Finally, the present invention provides, in combination with a column of elastomeric cord, a dispenser comprising container means providing the column of elastomeric cord; aperture means through which a free end of the column is fed; and cutter means affixed to the holder means for cutting the column withdrawn from the cord and passing through the aperture.

One exemplary stabilizing cord embodying the concepts of the present invention is disclosed in operative combination with a dental dam. The description of that embodiment is deemed sufficient to effect a full disclosure of the subject invention, the exemplary embodiment being shown by way of example in the accompanying drawings and being described in detail without attempting to show all the various forms and modifications in which the invention might be embodied—the invention being measured by the appended claims and not by the details of the specifications.

PREFERRED MODE FOR CARRYING OUT THE INVENTION

One representative form of a retention stabilizing means embodying the concepts of the present invention is designated generally by the numeral 10 on the accompanying drawings. The representative stabilizing cord 10 is depicted in operative association with a dental dam 11. Dental dam 11 comprises a flexible rubber sheet which can be stretched over a frame member 12. Such frames are known in the art as a Young frame and comprise a curved rim 13 that fits about the patient's jaw and opposed legs 14 and 15, somewhat perpendicular thereto. A plurality of radially extending tongs 16 are provided along the edge 18 thereof to engage the dam 11, which is stretched thereover. In the known art, depicted in FIG. 1, the dam 11 is retained over the teeth, in the patient's mouth by spring retainer clips 20 and 21. Clips 20 and 21 are stiff, expandable members having contact prongs 22 that are based against teeth e.g. molar $M_2$ and canine tooth $C_1$ where work is to be conducted on one or more of the teeth therebetween. Also depicted is a corner of rolled dental dam material 23, which has been wedged between molar $M_1$ and premolar $P_2$.

Figure 3:
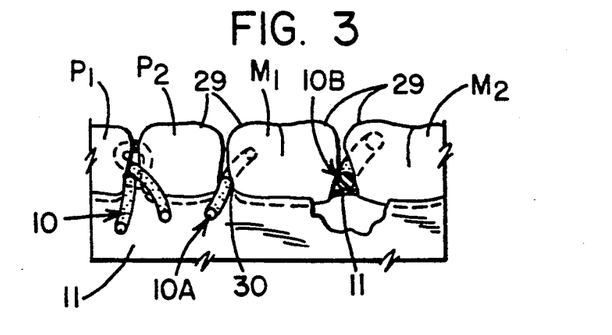
FIG. 3 is a partial side elevational view of the teeth depicted in FIG. 2 taken substantially along line 3—3 of FIG. 2.
Figure 5:
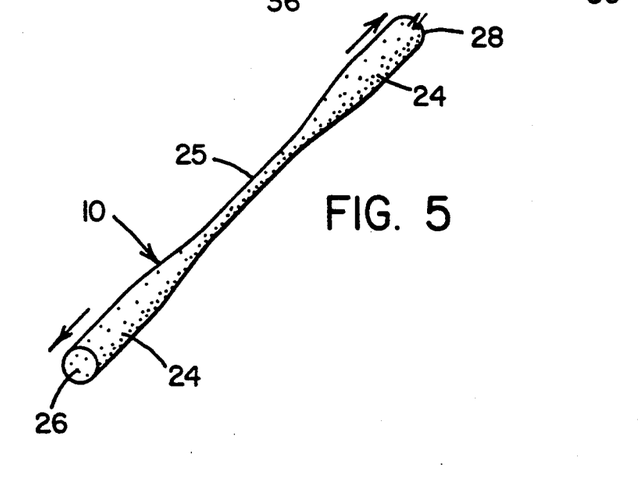
FIG. 5 is a perspective view of the elastomeric cord of the present invention, partially elongated.

With respect to the present invention, stabilizing cord 10 consists of a elastomeric, non-toxic strip of material such as natural rubber, thermoplastic elastomers and other high elongation, low hysteresis materials. A particularly useful material is natural rubber and is currently sold by the Assignee of record under the trademark WEDJETS. As best depicted in FIG. 5, upon application of a tensile force to the cord 10, which is necessary in order for the cord to be more easily slidably placed between two juxtaposed teeth, the cross-sectional area decreases from a first relaxed area 24 to a second elongated area 25. Generally, the decrease should be approximately 50 percent in diameter. Once the cord has been placed, the tensile force on ends 26 and 28 of cord 10 may be released and the cross-sectional area 25 expands between the two said juxtaposed teeth. As shown in FIG. 3, the expanded cord 10 will fill the area between the two tooth crowns 29, and the gingival mucosa 30, thereby supplying a force upwards against both tooth crowns 29, and downward against the dental dam 11 effecting retention and stabilization of the dental dam.

Figure 2:
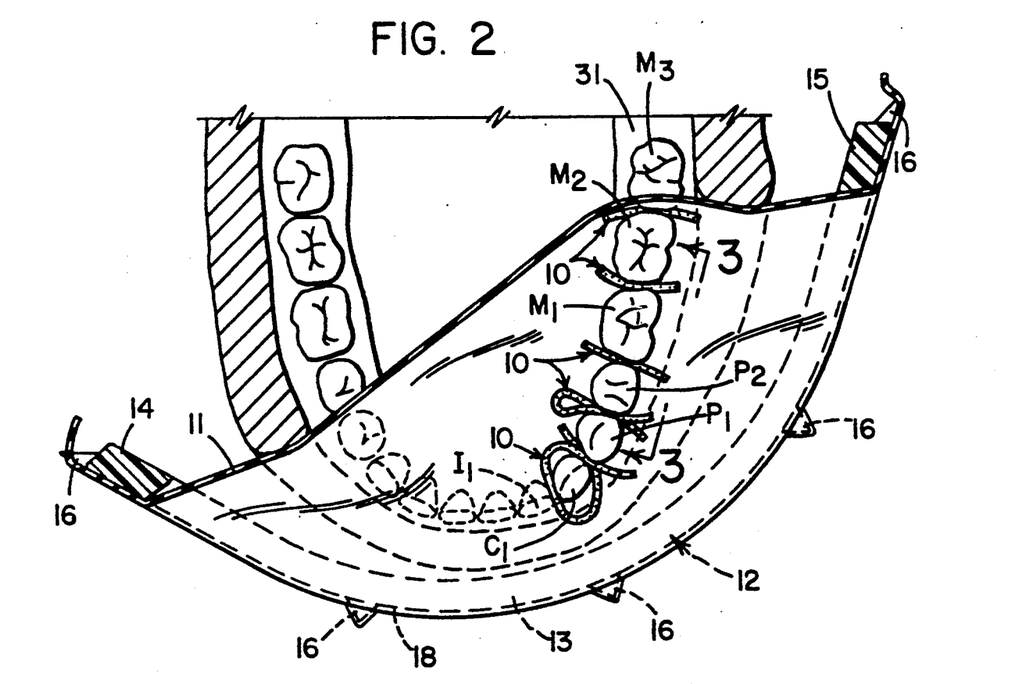
FIG. 2 is a top plan view of the teeth of the lower jaw depicting the elastomeric cord of the present invention employed in various methods and in operative association with a dental dam.

The method of the present invention is employed because passing the dam through the proximal tooth contact point is insufficient to secure the dam on the anchor tooth. With reference to FIG. 2, an exemplary embodiment is presented. Specifically, a section of cord member 10 is elongated by stretching and then interposed between molars $M_3$ and $M_2$ by urging downwardly therebetween. Upon release of cord 10, it expands from its second cross-sectional area 25 toward its first, greater cross-sectional area 24, which will not readily be dislodged from between the teeth, as clearly depicted in FIG. 3. A second section of cord 10 is interposed around canine tooth $C_1$, as and alternative placement technique, following which, operation on any of the teeth therebetween can be conducted.

Figure 4A:
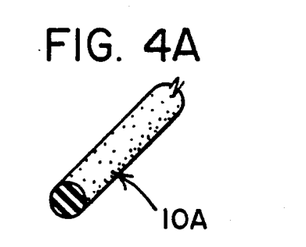
FIGS. 4A–4B are perspective views of the elastomeric cord of the present invention signifying the variance in size that may be employed.
Figure 4B:
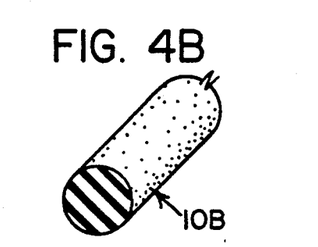

It is also to be noted that the present invention may be utilizing in most all tooth spacing arrangements inasmuch as differing diameters of the cord can be provided to fill larger or smaller tooth spaces as shown in FIGS. 4A and 4B. An exemplary embodiment is depicted in FIG. 3. The space between premolar $P_2$ and molar $M_1$ is narrow and, as a result, narrow cord 10A is employed. However, the space between molar $M_1$ and $M_2$ is larger requiring a cord with a larger cross-sectional area 10B to stabilize the dental dam 11.

In the event the largest diameter is still loose and the space appears more as a diastema, the cord 10 can be slidably interposed between two teeth, then, turned back upon itself and interposed between the same two juxtaposed teeth as shown in FIGS. 2 and 3 between premolars $P_1$ and $P_2$. A second anchor method that may be employed is depicted in FIG. 2 where cord 10 encircles canine tooth $C_1$ and after anchoring the dental dam 11 between premolar $P_1$ and $C_1$ a secondary anchor is created between the proximal side of canine tooth $C_1$ and the distal side of incisor tooth $I_1$. Cord 10 is then again interposed between $P_1$ and $C_1$. The effect of this anchor method is to maintain a double anchor between premolar $P_1$ and canine tooth $C_1$ while maintaining a secondary anchor between $C_1$ and Incisor $I_1$.

Figure 6:
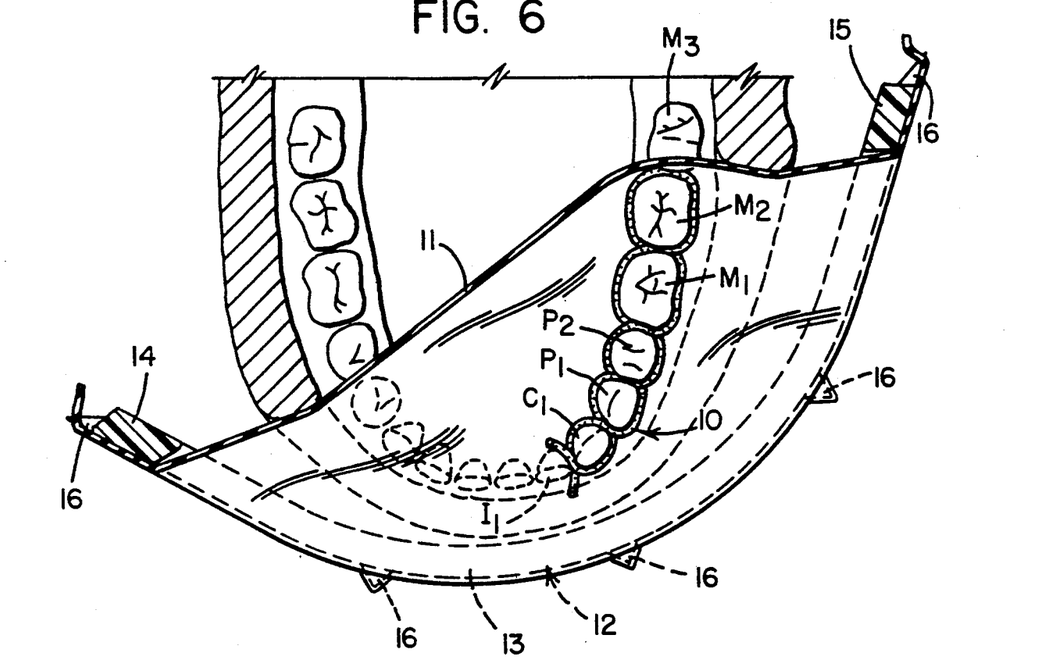
FIG. 6 is a top plan view of the teeth of the lower jaw depicting the elastomeric cord of the present invention employed in a woven "in-and-out" fashion and in operative association with a dental dam.

As is also depicted in FIGS. 2 and 3, the cord can be looped over and doubled over on itself between adjacent teeth ($P_1$ and $P_2$), depending upon the desires of the practitioner. Furthermore, a longer section could be "woven" in an in-and-out fashion between a plurality of teeth in the area of the mouth to be treated by the practitioner. As depicted in FIG. 6, after the dental dam 11 has been positioned over the teeth, a length of cord 10 is interposed between the first two teeth, $I_1$ and $C_1$ and is then past around the lingual (or buccal) side of $C_1$ to be interposed between the next two adjacent teeth, $C_1$ and $P_1$, this time being "woven" around the opposite, or buccal side of $P_1$. The practitioner continues the procedure in an alternating fashion between each two subsequent and adjacent teeth until reaching the last tooth of the area ($M_2$). At this tooth, the cord is encircled and is then re-interposed on opposite sides of the teeth, partially encircled during the first, alternating weave until the second tooth $C_1$, of said first two teeth has been encircled.

The practitioner may wish to utilize this method to provide a second moisture barrier. The cord would then act as a gasket eliminating any water that may creep up the tooth, past the dental dam, and into the work area. A second reason one may wish to utilize this method would be where extra retention is needed to complete the operation. This could be particularly true, for a patient with a diastema between many consecutive juxtaposed teeth.

Thus, it should be apparent to one skilled in the art that the use of stabilizing cord 10 can best be decided by the dentist at the time of the operative procedure, as each mouth will present different circumstances. Furthermore, it is to be understood that each new method employing cord 10 would fall within the scope of the present invention. However, the present invention cannot be employed if the area to be retained does not contain two juxtaposed teeth between which stabilizing cord 10 may be placed, as shown at 31 in FIG. 2.

The cord 10, being elastomeric, will reduce injury of the gingival tissue 30 because the tissue will force the cord 10 to deform, thereby applying pressure on the cord 10, instead of the cord 10 applying pressure on the tissue 30. However, to eliminate further any possible damage to tissue 30, various shapes can be employed. With reference to FIGS. 4D–4F, teardrop 10D, square 10E, and triangular 10F cross-sectional profiles are depicted. Such shapes will provide a body portion section 35 to extend and fill the gap between two juxtaposed teeth while providing a narrow trailing edge 36 for gingival tissue contact. The narrow trailing edge 36 will apply less pressure to the tissue 30 thereby causing less damage.

Figure 4C:
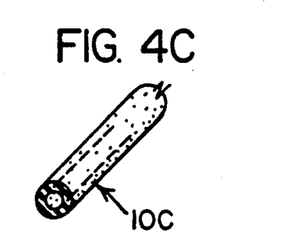
FIG. 4C is a perspective view of the elastomeric cord of the present invention with a substantially annular cross-section.
Figure 4D:
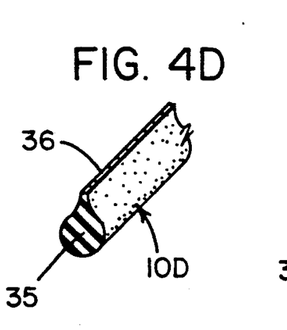
FIG. 4D is a perspective view of the elastomeric cord of the present invention with a substantially tear drop cross-section.
Figures 4E, 4F:
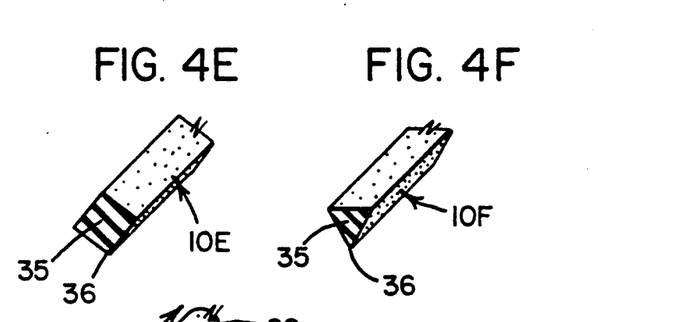
FIG. 4E is a perspective view of the elastomeric cord of the present invention with a substantially square cross-section.
FIG. 4F is a perspective view of the elastomeric cord of the present invention with a substantially triangular cross-section.

A further cross-section that may be employed further to eliminate any possible damage to tissue 30 is depicted in FIG. 4C and takes the form of a hollow or tubular filament 10C. Although an annular cross-section is depicted, it should be apparent that any of the aforementioned cross-sectional areas can be formed such that an axial cavity extends therethrough. The hollow stabilizing cord may be employed to provide a still narrower cross section.

Referring to FIG. 5, when a tensile force is applied to ends 26 and 28 of cord 10, for instance, a second narrower cross section 25 results. While actual diameters or cross sectional dimensions can vary, depending upon the needs of the practitioner, generally the narrower cross section should be up to about one-third of the relaxed, unelongated section of cord. This is true for solid cord, irrespective of the shape. For hollow cords, the ratio between relaxed and elongated dimensions may be greater.

Thus, when the cord itself is hollow, a narrower cross section 25 is provided than where cord is solid, thereby providing a stabilizing cord for employment between two juxtaposed teeth that are very close to each other. In conjunction with this benefit, it can be seen that because the cord is hollow, once it expands between the teeth, the same original cross section is provided on either side of the tooth. The hollow cord then allows for the cord to fit between closer teeth while still providing for full retention upon expansion. The hollow cord may also provide for a more forgiving cord to be utilized when the patient's mouth is abnormally sensitive. Having less material, the hollow cord will more easily be deformed. As a result, when the hollow cord is placed between two juxtaposed teeth, it will more readily deform thereby imparting less stress on the gingiva tissue. A third advantage is that because the cord will more easily be deformed, it will more readily accept the shape of the area between the teeth thereby acting to create a second, better, watertight seal.

Figure 1:
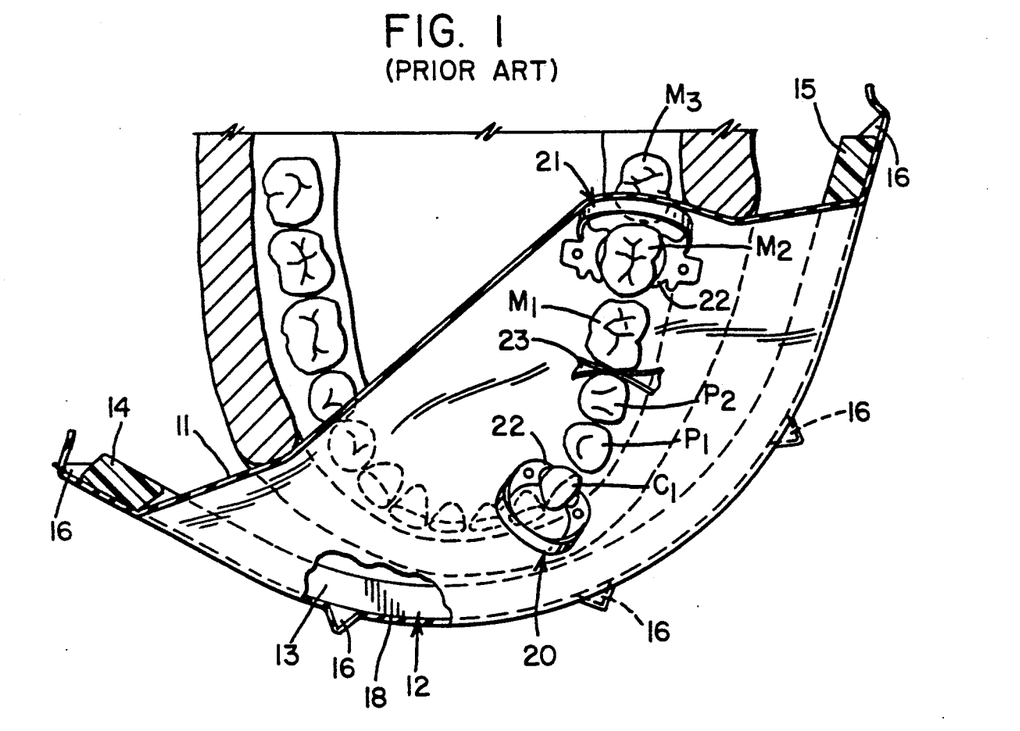
FIG. 1 is a top plan view of the teeth of the lower jaw depicting the prior art forms in operative association with a dental dam.

A further advantage of the present system is that the cord 10, whether hollow or solid, provides a retention system that is completely non-obtrusive in the work area. That is, once the dam is in place, the cord length can be adjusted by cutting away excesses so that only the cord between the teeth is acting to retain the dam with no extension into the work area. This differs from the prior art in that dam clamps 21 and 22 and the cut dam corner 23 extend into the work area.

Yet another advantage of the present system is the ease of employment. An assistant can easily insert the dental dam with the present invention as no skilled knotmaking is required. Furthermore, the patient does not need to be anesthetized to employ the present invention as with retention clamps of the prior art.

While the present invention provides an improvement in the field of dentistry, it is equally important for the cord to be readily dispensable from a convenient container. Generally, when the cord is randomly placed in a container and pulled through an aperture therein, the cord may twist or bind, possibly prohibiting further withdrawal. To eliminate the aforementioned problem, the cord is provided in a novel form, depicted in FIGS. 8 and 9. Specifically, the cord 10 is formed into a helical cylinder or column 40 which provides a single diameter of cord, coiled upon itself, and having a base 41 and a free end 42. As is apparent in FIG. 9, the helical configuration of column 40 provides a pitch substantially equal to the cord diameter, thereby defining a plurality of contiguous windings. At the juncture of each adjacent surface is a web 43, (FIG. 9) which holds the cord together in its columnar configuration.

Figures 8, 9:
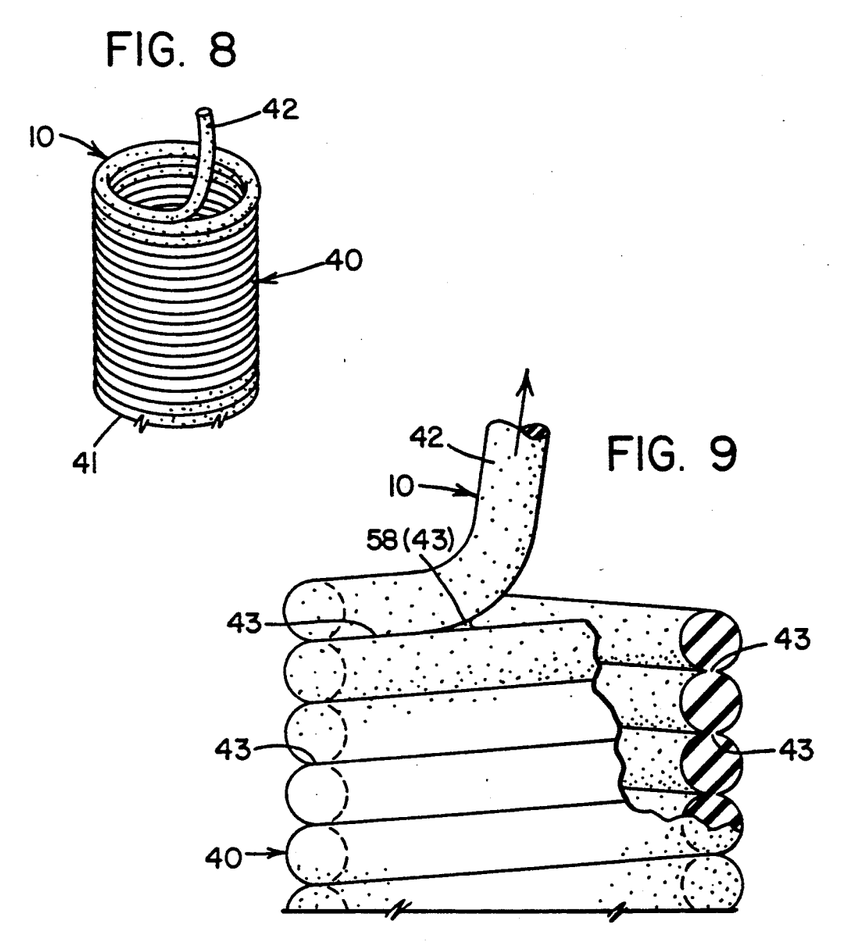
FIG. 8 is an perspective view of the webbed column.
FIG. 9 is an enlarged elevational view of a portion of the webbed column depicting first the web as it is broken upon the application of a force and also, in partial section, depicting the web as formed at the co-terminous boundary between windings.
Figure 10:
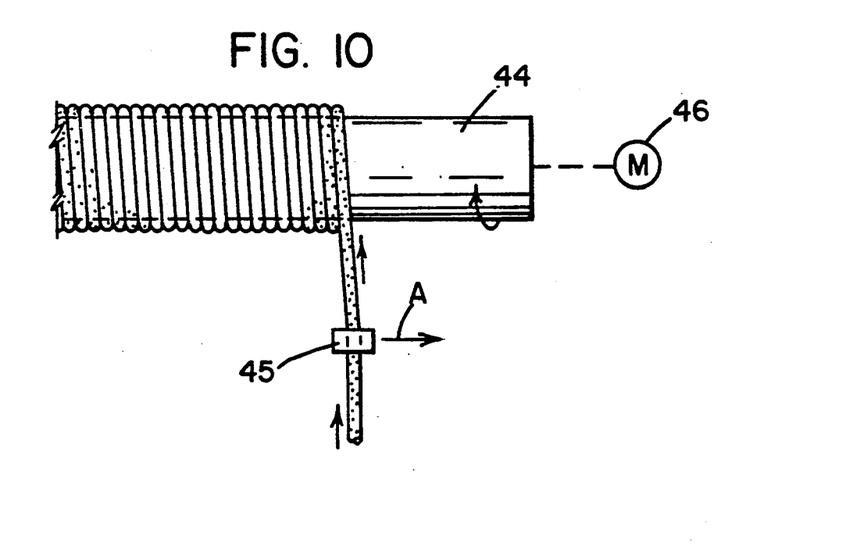
FIG. 10 is an elevational view of the manufacturing process creating the webbed column depicting the uncured elastomeric cord in operative association with a mandrel and feeder.

With reference to FIG. 10, manufacture of the cord column 40 is schematically depicted. The cord 10, in its uncured state, is wound onto a mandrel 44. The cord is first fed onto the mandrel 44 through a feeder 45. As the feeder 45 slowly moves in the direction of arrow A, mandrel 44 is rotated by a motor 46 and the cord 10 is wound around the mandrel at a rate whereby each winding has a pitch substantially equal to the cord diameter. Once the cord is wound onto the mandrel 44, it is heated and allowed to cool. Upon cooling, each successive winding will adhere to the windings adjacent thereto, thereby creating a coil, or column 40. The windings adhere to each other in the manner previously described in FIG. 10, to form the web 43 which is created when the material cures. The web inhibits the unwinding of the column which can then be removed from the mandrel 44 and cut into a freestanding unit of predetermined length, again as depicted in FIG. 8.

Figure 7:
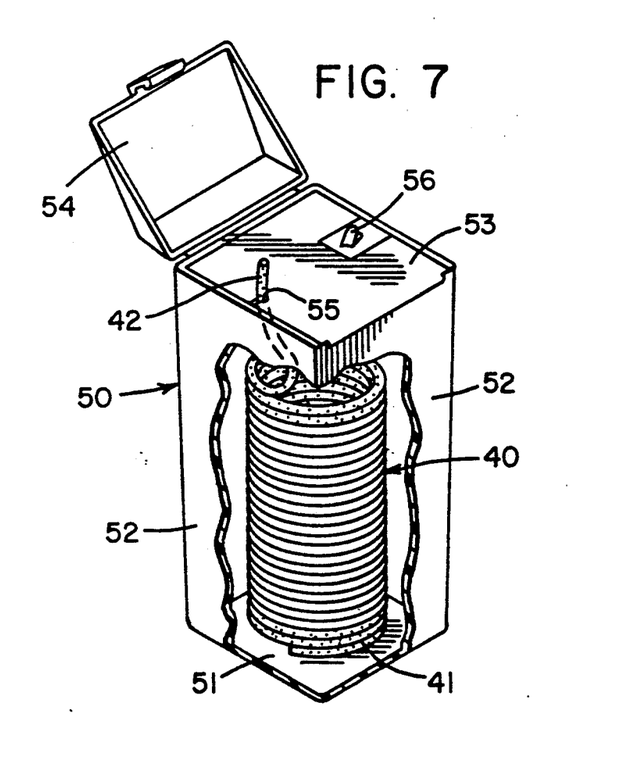
FIG. 7 is a perspective view of the webbed column created from the elastomeric cord of the present invention being viewed through a partial cut-away of the packaging box enveloping the column.

The coil or column 40 is then placed inside of a standard container 50 having a base 51, sides 52, top 53 and removable cover 54. An aperture 55 is provided in the top 53, or in the center (not shown) or out one of the sides 52 (also not shown). A metal cutter 56 can be carried by the top 53 to sever predetermined lengths of cord 10.

The free end 42 as fed through the aperture 55 for withdrawal of the cord from column 40. During use, a tensile force sufficient to break the web bond at 58 will be applied and as it is applied, the web will continue to pull apart thereby freeing the top winding of the column 40 so that it can be pulled through aperture 55 without binding. The column 40 may rotate within the container, although this is not a necessary condition. While the present embodiment depicts the aperture in the edge of the container top 53, it should be apparent to one skilled in the art that the aperture may be placed in any position on the container that allows for the material to be drawn off the top of the column 40.

It should be appreciated that the column 40 could be formed via other techniques including but not limited to the use of volatile solvents, adhesives compositions and the like so as to provide the necessary integrity to form a column and a tearing action of the free end 42 from the column 40. It should also be apparent that while the present exemplary embodiment depicts the coil created from a cord having a circular-cross section, any cross-section may be employed without departing from the spirit of the present invention.

Based upon the foregoing description, it should be apparent that a method and elastomeric cord embodying the concepts of the present invention effectively secure the dental dam in place. It should also be apparent to one skilled in the art that the cross-sectional shape and area may be altered beyond that which has been discussed herein without departing from the spirit of the present invention. The cord is not limited to a particular rubber composition; nor, is the manufacture of the column limited to the methods disclosed herein. Finally, it is to be understood that the dispensing container can be varied within the spirit of the present invention provided that it remains operable with the cord 10.

It is also evident that all variations fall within the scope of the claimed invention; therefore, the selection of specific material components as well as method steps can be determined without departing from the spirit of the present invention. Moreover, the scope of the present invention shall include all modifications and variations that may fall within the scope of the attached claims.

I claim:

1. A method for retaining a dental dam comprising the steps of:
    positioning a dental dam over a plurality of teeth in the mouth of a patient;
    selecting a section of elastomeric cord;
    elongating said section to reduce the cross-sectional area thereof;
    interposing a portion of said elongated section between at least two adjacent teeth and over said dam; and allowing said section to expand toward its original cross-sectional area thereby prohibiting the removal of said dam from said teeth.

2. A method, as set forth in claim 1, including the additional step of looping a second portion of said elongated section between said two adjacent teeth.

3. A method, as set forth in claim 1, including the additional step of looping a second portion of said elongated section between one of said two adjacent teeth and a third tooth, adjacent thereto.

4. A method, as set forth in claim 1, including the additional step of trimming excess length from said section after said step of allowing.

5. A method, as set forth in claim 1, including the additional steps of:
  repeatedly elongating a portion of said cord;
  interposing said elongated portion between a plurality of successive, adjacent teeth, alternating between lingual and buccal sides of successive teeth;
  encircling the last of said plurality of teeth; and
  re-interposing said elongated portion between said teeth, contacting the lingual side of each tooth previously contacted on the buccal side and the buccal side of each tooth previously contacted on the lingual side until the second of said at least two adjacent teeth has been encircled.

6. In combination with a dental dam having a plurality of individual holes to fit over a like plurality of teeth in the mouth of a patient,
  an elastomeric cord, separate from said dam having a first cross-sectional area at relaxation and a second cross-sectional area at elongation of lesser dimension than said first, said second cross-sectional area being interposed between a pair of adjacent teeth when placed therebetween and over said dam in position with respect to said teeth, wherein said second cross-sectional area expands to said first cross-sectional area and forms an elastomeric wedge between said teeth to retain said dam.

7. The combination, as set forth in claim 6, further comprising frame means positionable about the jaw of a patient, providing tangs engageable with said dam.

8. The combination, as set forth in claim 6, wherein said first and second cross-sectional areas are circular.

9. The combination, as set forth in claim 6, wherein said first and second cross-sectional areas are triangular.

10. The combination, as set forth in claim 6, wherein said first and second cross-sectional areas are teardrop-shaped.

11. The combination, as set forth in claim 6, wherein said first and second cross-sectional areas are square.

12. The combination, as set forth in claim 6, wherein said first and second cross-sectional areas are annular having an outer and inner diameter.

* * * * *

UNITED STATES PATENT AND TRADEMARK OFFICE
CERTIFICATE OF CORRECTION

PATENT NO. : 5,104,317
DATED : April 14, 1992
INVENTOR(S) : John Riazi

It is certified that error appears in the above-identified patent and that said Letters Patent is hereby corrected as shown below:

Column 5, line 11 "Fig. 5" should read "Fig. 6"

Signed and Sealed this

Seventeenth Day of January, 1995

Attest:

BRUCE LEHMAN

Attesting Officer

Commissioner of Patents and Trademarks